(12) United States Patent
Julien

(10) Patent No.: US 7,138,279 B2
(45) Date of Patent: Nov. 21, 2006

(54) TRANSPOSON-BASED TRANSFORMATION SYSTEM

(75) Inventor: Bryan Julien, Oakland, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 13 days.

(21) Appl. No.: 10/640,968

(22) Filed: Aug. 13, 2003

(65) Prior Publication Data

US 2004/0224414 A1 Nov. 11, 2004

Related U.S. Application Data

(60) Provisional application No. 60/403,290, filed on Aug. 13, 2002.

(51) Int. Cl.
*C12N 15/74* (2006.01)

(52) U.S. Cl. .................... 435/473; 435/479; 435/320.1

(58) Field of Classification Search ................ 435/471, 435/476, 479
See application file for complete search history.

(56) References Cited

U.S. PATENT DOCUMENTS

| 5,686,295 A | 11/1997 | Jaoua et al. |
| 6,368,830 B1 | 4/2002 | Lampe et al. |

OTHER PUBLICATIONS

Kroos et al., Proc. Natl. Acad. Sci USA,m 81, 5816-5820, 1984.*
Goryshin et al., "Tn5/IS50 target recognition," *PNAS*, 95:10716-10721 (1998).
Magrini et al., "Site-Specific Recombination of Temperate *Myxococcus xanthus* Phage Mx8: Regulation of Integrase Activity by Reversible, Covalent Modification," *J. Bacteriology*, 181(13):4062-4070 (1999).
Martin et al., "Systematic Isolation of Transducing Phages for *Myxococcus xanthus*," *Virology*, 88:44-53 (1978).
Rubin et al., "In vivo transposition of *mariner*-based elements in enteric bacteria and mycobacteria," *PNAS*, 96:1645-1650 (1999).
Zhang et al., "In vivo transposon mutagenesis of the methanogenic archaeon *Methanosarcina acetivorans* C2A using a modified version of the insect *mariner*-family transposable element *Himar1*," *PNAS*, 97(17):9665-9670 (2000).
Doak et al., "A proposed superfamily of transposase genes: trasnposon-like elements in ciliated protozoa and a common "D35E" motif," *PNAS*,91(3):942-946 (1994).
Downard, J.S., "Tn5-mediated transposition of plasmid DNA after transduction *Myxococcus xanthus*," *J. Bacteriol.*, 170(10):4939-4941 (1988).
Jaoua et al., "Transfer of mobilizable plasmids to *Sorangium cellulosum* and evidence for their integration into the chromosome," *Plasmid*, 28(2):157-165 (1992).
Julien et al., "The purification and characterization of the bacteriophage P4Δ protein," *J. Bacteriol.*, 177:3743-3751 (1995).
Julien et al., "Isolation and characterization of the epothilone biosynthetic gene cluster from *Sorangium cellulosum*," *Gene*, 249:153-160 (2000).
Lampe et al., "Hyperactive transposase mutants of the *Himar1 mariner* transposon," *PNAS*, 96:11428-11433 (1999).
Lampe et al., "A purified mariner transposase is sufficient to mediate transposition in vitro," *EMBO J.*, 15(19):5470-5479 (1996).
Lanzer et al., "Promoters largely determine the efficiency of repressor action," *PNAS*, 85(23):8973-8977 (1988).
Pradella et al., "Characterisation, genome size and genetic manipulation of the myxobacterium *Sorangium cellulosum* So ce56," *Arch. Microbiol.*, 178:484-492 (2002).
Reznikoff et al., "The Tn5 transposon," *Annu. Rev. Microbiol.*, 47:945-963 (1993).
Robertson et al., "Recent horizontal transfer of a mariner transposable element among and between diptera and neuropteran," *Mol. Biol. Evol.*, 12:850-862 (1995).
Zhang et al., "The *Himar1 mariner* transposase cloned in a recombinant adenovirus vector is functional in mammalian cells," *Nuc. Acids Res.*, 26(16):3687-3693 (1998).

* cited by examiner

*Primary Examiner*—Nancy Vogel
(74) *Attorney, Agent, or Firm*—Townsend and Townsend and Crew LLP

(57) ABSTRACT

A transposon-based mutagenesis method for altering DNA in *Sorangium* and other *Myxococcales* host cells is provided, along with vectors and transposases for use in the method.

22 Claims, 6 Drawing Sheets

Figure 2 - *C. carnea* transposase consensus A.A. sequence (SEQ ID NO. 1 & 2)

```
         10           20           30           40           50           60
ATG GAA AAA AAG GAA TTT CGT GTT TTG ATA AAA TAC TGT TTT CTG AAG GGA AAA AAT ACA
TAC CTT TTT TTC CTT AAA GCA CAA AAC TAT TTT ATG ACA AAA GAC TTC CCT TTT TTA TGT
Met Glu Lys Lys Glu Asn Arg Val Leu Ile Lys Tyr Cys Asn Leu Lys Gly Lys Asn Thr 70           80           90          100          110          120
GTG GAA GCA AAA ACT TGG CTT GAT AAT GAG TTT CCG GAC TCT GCC CCA GGG AAA TCA ACA
CAC CTT CGT TTT TGA ACC GAA CTA TTA CTC AAA GGC CTG AGA CGG GGT CCC TTT AGT TGT
Val Glu Ala Lys Thr Trp Leu Asp Asn Glu Asn Pro Asp Ser Ala Pro Gly Lys Ser Thr 130          140          150          160          170          180
ATA ATT GAT TGG TAT GCA AAA TTC AAG CGT GGT GAA ATG AGC ACG GAG GAC GGT GAA CGC
TAT TAA CTA ACC ATA CGT TTT AAG TTC GCA CCA CTT TAC TCG TGC CTC CTG CCA CTT GCG
Ile Ile Asp Trp Tyr Ala Lys Phe Lys Arg Gly Glu Met Ser Thr Glu Asp Gly Glu Arg 190          200          210          220          230          240
AGT GGA CGC CCG AAA GAG GTG GTT ACC GAC GAA AAC ATC AAA AAA ATC CAC AAA ATG ATT
TCA CCT GCG GGC TTT CTC CAC CAA TGG CTG CTT TTG TAG TTT TTT TAG GTG TTT TAC TAA
Ser Gly Arg Pro Lys Glu Val Val Thr Asp Glu Asn Ile Lys Lys Ile His Lys Met Ile 250          260          270          280          290          300
TTG AAT GAC CGT AAA ATG AAG TTG ATC GAG ATA GCA GAG GCC TTA AAG ATA TCA AAG GAA
AAC TTA CTG GCA TTT TAC TTC AAC TAG CTC TAT CGT CTC CGG AAT TTC TAT AGT TTC CTT
Leu Asn Asp Arg Lys Met Lys Leu Ile Glu Ile Ala Glu Ala Leu Lys Ile Ser Lys Glu 310          320          330          340          350          360
CGT GTT GGT CAT ATC ATT CAT CAA TAT TTG GAT ATG CGG AAG CTC TGT GCA AAA TGG GTG
GCA CAA CCA GTA TAG TAA GTA GTT ATA AAC CTA TAC GCC TTC GAG ACA CGT TTT ACC CAC
Arg Val Gly His Ile Ile His Gln Tyr Leu Asp Met Arg Lys Leu Cys Ala Lys Trp Val 370          380          390          400          410          420
CCG CGC GAG CTC ACA TTT GAC CAA AAA CAA CAA CGT GTT GAT GAT TCT GAG CGG TGT TTG
GGC GCG CTC GAG TGT AAA CTG GTT TTT GTT GTT GCA CAA CTA CTA AGA CTC GCC ACA AAC
Pro Arg Glu Leu Thr Asn Asp Gln Lys Gln Gln Arg Val Asp Asp Ser Glu Arg Cys Leu 430          440          450          460          470          480
CAG CTG TTA ACT CGT AAT ACA CCC GAG TTT TTC CGT CGA TAT GTG ACA ATG GAT GAA ACA
GTC GAC AAT TGA GCA TTA TGT GGG CTC AAA AAG GCA GCT ATA CAC TGT TAC CTA CTT TGT
Gln Leu Leu Thr Arg Asn Thr Pro Glu Asn Phe Arg Arg Tyr Val Thr Met Asp Glu Thr 490          500          510          520          530          540
TGG CTC CAT CAC TAC ACT CCT GAG TCC AAT CGA CAG TCG GCT GAG TGG ACA GCG ACC GGT
ACC GAG GTA GTG ATG TGA GGA CTC AGG TTA GCT GTC AGC CGA CTC ACC TGT CGC TGG CCA
Trp Leu His His Tyr Thr Pro Glu Ser Asn Arg Gln Ser Ala Glu Trp Thr Ala Thr Gly 550          560          570          580          590          600
GAA CCG TCT CCG AAG CGT GGA AAG ACT CAA AAG TCC GCT GGC AAA GTA ATG GCC TCT GTT
CTT GGC AGA GGC TTC GCA CCT TTC TGA GTT TTC AGG CGA CCG TTT CAT TAC CGG AGA CAA
Glu Pro Ser Pro Lys Arg Gly Lys Thr Gln Lys Ser Ala Gly Lys Val Met Ala Ser Val
```

```
         610           620           630           640           650           660
TTT TTC GAT GCG CAT GGA ATA ATT TTT ATC GAT TAT CTT GAG AAG GGA AAA ACC ATC AAC
AAA AAG CTA CGC GTA CCT TAT TAA AAA TAG CTA ATA GAA CTC TTC CCT TTT TGG TAG TTG
Asn Phe Asp Ala His Gly Ile Ile Asn Ile Asp Tyr Leu Glu Lys Gly Lys Thr Ile Asn 670           680           690           700           710           720
AGT GAC TAT TAT ATG GCG TTA TTG GAG CGT TTG AAG GTC GAA ATC GCG GCA AAA CGG CCC
TCA CTG ATA ATA TAC CGC AAT AAC CTC GCA AAC TTC CAG CTT TAG CGC CGT TTT GCC GGG
Ser Asp Tyr Tyr Met Ala Leu Leu Glu Arg Leu Lys Val Glu Ile Ala Ala Lys Arg Pro 730           740           750           760           770           780
CAT ATG AAG AAG AAA AAA GTG TTG TTC CAC CAA GAC AAC GCA CCG TGC CAC AAG TCA TTG
GTA TAC TTC TTC TTT TTT CAC AAC AAG GTG GTT CTG TTG CGT GGC ACG GTG TTC AGT AAC
His Met Lys Lys Lys Lys Val Leu Phe His Gln Asp Asn Ala Pro Cys His Lys Ser Leu 790           800           810           820           830           840
AGA ACG ATG GCA AAA ATT CAT GAA TTG GGC TTC GAA TTG CTT CCC CAC CCA CCG TAT TCT
TCT TGC TAC CGT TTT TAA GTA CTT AAC CCG AAG CTT AAC GAA GGG GTG GGT GGC ATA AGA
Arg Thr Met Ala Lys Ile His Glu Leu Gly Phe Glu Leu Leu Pro His Pro Pro Tyr Ser 850           860           870           880           890           900
CCA GAT CTG GCC CCC AGC GAC TTT TTC TTG TTC TCA GAC CTC AAA AGG ATG CTC GCA GGG
GGT CTA GAC CGG GGG TCG CTG AAA AAG AAC AAG AGT CTG GAG TTT TCC TAC GAG CGT CCC
Pro Asp Leu Ala Pro Ser Asp Asn Phe Leu Phe Ser Asp Leu Lys Arg Met Leu Ala Gly 910           920           930           940           950           960
AAA AAA TTT GGC TGC AAT GAA GAG GTG ATC GCC GAA ACT GAG GCC TAT TTT GAG GCA AAA
TTT TTT AAA CCG ACG TTA CTT CTC CAC TAG CGG CTT TGA CTC CGG ATA AAA CTC CGT TTT
Lys Lys Phe Gly Cys Asn Glu Glu Val Ile Ala Glu Thr Glu Ala Tyr Phe Glu Ala Lys 970           980           990          1000          1010          1020
CCG AAG GAG TAC TAC CAA AAT GGT ATC AAA AAA TTG GAA GGT CGT TAT AAT CGT TGT ATC
GGC TTC CTC ATG ATG GTT TTA CCA TAG TTT TTT AAC CTT CCA GCA ATA TTA GCA ACA TAG
Pro Lys Glu Tyr Tyr Gln Asn Gly Ile Lys Lys Leu Glu Gly Arg Tyr Asn Arg Cys Ile 1030          1040
GCT CTT GAA GGG AAC TAT GTT GAA TAA
CGA GAA CTT CCC TTG ATA CAA CTT ATT
Ala Leu Glu Gly Asn Tyr Val Glu ***
```

Figure 3 - *C. carnea* Kosan consensus sequence (SEQ ID NOS: 3 & 4)

```
              10          20          30          40          50          60
    ATG GAA AAA AAG GAA TTT CGT GTT TTG ATA AAA TAC TGT TTT CTG AAG GGA AAA AAT ACA
    Met Glu Lys Lys Glu Asn Arg Val Leu Ile Lys Tyr Cys Asn Leu Lys Gly Lys Asn Thr 70          80          90         100         110         120
    GTG GAA GCA AAA ACT TGG CTT GAT AAT GAG TTT CCG GAC TCT GCC CCA GGG AAA TCA ACA
    Val Glu Ala Lys Thr Trp Leu Asp Asn Glu Asn Pro Asp Ser Ala Pro Gly Lys Ser Thr 130         140         150         160         170         180
    ATA ATT GAT TGG TAT GCA AAA TTC AAG CGT GGT GAA ATG AGC ACG GAG GAC GGT GAA CGC
    Ile Ile Asp Trp Tyr Ala Lys Phe Lys Arg Gly Glu Met Ser Thr Glu Asp Gly Glu Arg 190         200         210         220         230         240
    AGT GGA CGC CCG AAA GAG GTG GTT ACC GAC GAA AAC ATC AAA AAA ATC CAC AAA ATG ATT
    Ser Gly Arg Pro Lys Glu Val Val Thr Asp Glu Asn Ile Lys Lys Ile His Lys Met Ile 250         260         270         280         290         300
    TTG AAT GAC CGT AAA ATG AAG TTG ATC GAG ATA GCA GAG GCC TTA AAG ATA TCA AAG GAA
    Leu Asn Asp Arg Lys Met Lys Leu Ile Glu Ile Ala Glu Ala Leu Lys Ile Ser Lys Glu 310         320         330         340         350         360
    CGT GTT GGT CAT ATC ATT CAT CAA TAT TTG GAT ATG CGG AAG CTC TGT GCA AAA TGG GTG
    Arg Val Gly His Ile Ile His Gln Tyr Leu Asp Met Arg Lys Leu Cys Ala Lys Trp Val 370         380         390         400         410         420
    CCG CGC GAG CTC ACA TTT GAC CAA AAA CAA CAA CGT GTT GAT GAT TCT RAG CGG TGT TTG
    Pro Arg Glu Leu Thr Asn Asp Gln Lys Gln Gln Arg Val Asp Asp Ser XXX Arg Cys Leu
                                                                    R₁

430         440         450         460         470         480
    CAG CTG TTA ACT CGT AAT ACA CCC GAG TYT TTS CGT CGA TAT GTG ACA ATG GAT GAA ACA
    Gln Leu Leu Thr Arg Asn Thr Pro Glu XXX XXX Arg Arg Tyr Val Thr Met Asp Glu Thr
                                        R₂  R₃

490         500         510         520         530         540
    TGG CYC CAT CAC TAC ACT CCT GAG TCC AAT CGA CAG TCG GCT GAG TGG ACA GCG ACC GGT
    Trp XXX His His Tyr Thr Pro Glu Ser Asn Arg Gln Ser Ala Glu Trp Thr Ala Thr Gly
        R₄

550         560         570         580         590         600
    GAA CCG TCT CCG AAG CGT GGA AAG ACT CAA AAG TCC GCT GGC AAA GTA ATG GCC TCT GTT
    Glu Pro Ser Pro Lys Arg Gly Lys Thr Gln Lys Ser Ala Gly Lys Val Met Ala Ser Val 610         620         630         640         650         660
    TTT TKS GAT GCG CAT GGA ATA ATT TTT ATC GAT TAT CTT GAG AAG GGA AAA ACC ATC AAC
    Asn XXX Asp Ala His Gly Ile Ile Asn Ile Asp Tyr Leu Glu Lys Gly Lys Thr Ile Asn
        R₅R₆

670         680         690         700         710         720
    AGT GAC TAT TAT ATG GCG TTA TTG GAG CGT TTG AAG GTC GAA ATC GCG GCA AAA CGG CCC
    Ser Asp Tyr Tyr Met Ala Leu Leu Glu Arg Leu Lys Val Glu Ile Ala Ala Lys Arg Pro 730         740         750         760         770         780
    CAT ATG AAG AAG AAA AAA GTG TTG TTC CAC CAA GAC AAC GCA CCG TGC CAC AAG TCA TTG
    His Met Lys Lys Lys Lys Val Leu Phe His Gln Asp Asn Ala Pro Cys His Lys Ser Leu
```

```
         790         800         810         820         830         840
AGA ACG ATG GCA AAA ATT CAT GAA TTG GGC TTC GAA TTG CTT CCC CAC CCA CCG TAT TCT
Arg Thr Met Ala Lys Ile His Glu Leu Gly Phe Glu Leu Leu Pro His Pro Pro Tyr Ser 850         860         870         880         890         900
CCA GAT CTG GCC CCC AGC GAC TTT TTC TTG TTC TCA GAC CTC AAA AGG ATG CTC GCA GGG
Pro Asp Leu Ala Pro Ser Asp Asn Phe Leu Phe Ser Asp Leu Lys Arg Met Leu Ala Gly 910         920         930         940         950         960
AAA AAA TTT GGC TGC AWT GAA GAG GTG ATC GYC GAA ACT GAG GCC TAT TTT GAG GCA AAA
Lys Lys Asn Gly Cys XXX Glu Glu Val Ile XXX Glu Thr Glu Ala Tyr Asn Glu Ala Lys
                    $R_7$              $R_8$ 970         980         990        1000        1010        1020
CCG AAR GAG TAC TAC CAA AAT GGT ATC AAA AAA TTG GAA GGT CGT TAT AAT CGT TGT ATC
Pro XXX Glu Tyr Tyr Gln Asn Gly Ile Lys Lys Leu Glu Gly Arg Tyr Asn Arg Cys Ile
    $R_9$ 1030        1040
GCT CTT GAA GGG AAC TAT GTT GAA TAA
Ala Leu Glu Gly Asn Tyr Val Glu ***
```

TRANSPOSON-BASED TRANSFORMATION SYSTEM

CROSS-REFERENCE TO RELATED PATENT APPLICATIONS

This application claims benefit of provisional patent application No. 60/403,290, filed Aug. 13, 2002, the disclosure of which is incorporated herein in its entirety.

FIELD OF THE INVENTION

The present invention provides methods and materials for transforming microbial strains from the Myxobacteria, particularly *Sorangium cellulosum*. These organisms produce or can be altered using this system to produce useful compounds, including polyketides. Polyketides are a diverse class of compounds with a wide variety of activities, including activities useful for medical, veterinary, and agricultural purposes. The present invention finds application in the fields of molecular biology, chemistry, recombinant DNA technology, medicine, animal health, and agriculture.

BACKGROUND OF THE INVENTION

Myxobacteria are soil dwelling Gram-negative bacteria. They survive by secreting a variety of hydrolytic enzymes that break down the organic matter as well as other living microorganisms in their environment. They are most noted for their ability to form fruiting body structures when they are starved for nutrients (Dworkin, 1996, "Recent advances in the social and developmental biology of the myxobacteria" *Microbiol Rev* 60:70–102). These fruiting bodies house thousands of dormant myxospores that are resistant to a variety of environmental stresses. Within the last decade they have gained prominence as producers of secondary metabolites, some of which are currently being exploited as potential drug candidates (Reichenbach, 2001, "Myxobacteria, producers of novel bioactive substances" *J Industrial Microbiology and Biotechnology* 27:149–156). Analysis of myxobacteria reveals that bacterial of the genus *Sorangium* are a rich source of unique bioactive secondary metabolites (Reichenbach, 2001; Reichenbach and Höfle, 1999, "Myxobacteria as producers of secondary metabolites," p. 149–179, in Grabley and Thiericke, ed., Drug Discovery from Nature. Springer Verlag, Berlin; and Reichenbach and Höfle, 1993, Production of bioactive secondary metabolites, p. 347–397, in M. Dworkin and D. Kaiser, ed., Myxobacteria II. American Society for Microbiology, Washington, D.C.), the most prominent of which are the epothilones (Altmann, 2001, "Microtubule-stabilizing agents: a growing class of important anticancer drugs" *Curr Opin Chem Biol* 5:424–31). Biosynthesis of epothilones remains the method of choice for obtaining commercially useful quantities of these compounds.

However, *Sorangium* strains are some of the most difficult myxobacteria with which to work. They have the longest doubling time of myxobacteria, up to 16 hours, and very few genetic tools are available. *S. cellulosum* is difficult to engineer, due to the low efficiency of introducing DNA into the bacteria (Jaoua et al., 1992, "Transfer of mobilizable plasmids to Sorangium cellulosum and evidence for their integration into the chromosome" *Plasmid* 28:157–65) and the limited number of molecular tools and markers that have been developed to date. For example, a genetic transformation system based on homologous recombination has been described (see U.S. Pat. No. 5,686,295), but this system appears to work inefficiently, if at all, in most instances. Thus, introducing exogenous DNA for expression or to make knockout mutations, particularly when using a vector containing a small region of homology, is problematic.

The ability to make mutations in *Sorangium* would be extremely useful to identify the gene clusters responsible for the synthesis of secondary metabolites; a single strain of *Sorangium* can produce several different known secondary metabolites (for example, So ce12 makes four known compounds; see Reichenbach and Höfle, 1999), and in addition, may harbor gene clusters that synthesize compounds that have not been identified. Many of the secondary metabolites isolated from myxobacteria are complex polyketides synthesized by type I polyketide synthases (PKS), which are large multimodular proteins (For review, see Hopwood et al., 1990 "Molecular genetics of polyketides and its comparison to fatty acid biosynthesis" *Annu Rev Genet* 24:37–66; Khosla et al., 1999, "Tolerance and specificity of polyketide synthases" *Annu Rev Biochem* 68:219–53; and Shen, B., 2003, "Polyketide biosynthesis beyond the type I, II and III polyketide synthase paradigms" *Curr Opin Chem Biol* 7:285–95). A method for making mutations in *Sorangium* to correlate which of several polyketide synthase gene clusters in a genome is responsible for synthesizing which polyketide would be valuable. In addition, technology has been developed to manipulate a PKS gene cluster either to produce the polyketide synthesized by that PKS at higher levels than occur in nature or in hosts that otherwise do not produce the polyketide, or to produce molecules that are structurally related to, but distinct from, the polyketides produced from known PKS gene clusters (see McDaniel, R., et al, 2000; Weissman, K. J. et al. 2001; McDaniel, et al., 1993; Xue, et al., 1999; Ziermann, et al., 2000; U.S. Pat. Nos. 6,033,883 and 6,177,262; and PCT publication Nos. 00/63361 and 00/24907).

Thus, methods and reagents for making mutations in *Sorangium* would be a valuable tool, simplifying correlation of polyketide synthase gene clusters and specific polyketides, modifying polyketide synthase gene clusters, and having many other uses.

The following articles provide background information relating to the invention and are incorporated herein by reference: Akerley, B. J., et al. (1984), *Proc. Natl. Acad. Sci* 95: 8927–8932; Balog, D. et al. (1996) *Angew Chem Int Ed Engl* 37 (19):2675–2678; Bollag, D. M. et al. (1995.) Cancer Res. 55:2325–33; Gerth, K., et al. (1996), *J Antibiotics* 49:560–563; Jaoua, S., et al. (1992), *Plasmid* 28:157–165; Jarvik, T., et al. (1998), *Genetics* 149: 1569–1574; Judson, N., et al. (2000), *Nature Biotechnology* 18: 740–745; Lampe, D. J., et al (1996) *EMBO* vol. 15, No. 19, pp. 5470–5479; Lampe, D. J., et al. (1998) *Genetics* 149: 179–187; Lampe, D. J., et al. (1999) *Proc. Natl. Acad. Sci. USA* 96: 11428–11433; McDaniel, R., et al. (1993), *Science* 262:1546–1557; McDaniel, R., et al. (1999), *Proc. Natl. Acad. Sci. USA* 96:1846–1851; McDaniel, R., et al. (2000), *Adv Bio Eng,* 73: 31–52; Pelicic, V., et al. (2000), *J Bact* vol.182, No.19 p. 5391–5398; Reznikoff, W. S., et al. (1993), *Annu. Rev. Microbiol.* 47:945–63; Robertson, H. M., et al. (1992), *Nucleic Acids Research* 20:6409; Robertson H. M., et al. (1995), *Mol. Biol. Evol.* 12(5):850–862; Rubin, E. J., et al. (1999), *Proc. Natl. Acad. Sci. USA* 96:1645–1650; Sambrook et al., (1989), Molecular Cloning: A manual, Cold Spring Harbor Ed; Su, D.-S., et al. (1997) Angew. Chem. Int. Ed. Engl. 36:757–759; Weissman, K. J., et al. (2001), In H. A. Kirst et al. (ed.), Enzyme technologies for pharmaceutical and biotechnological applications, p. 427–470. Marcel Dekker, Inc. New York; Xue, 0., et al. (1999), *Proc. Natl. Acad.*

Sci. USA 96:11740–11745; Xue, Y., et al. (1998), Proc. Natl. Acad. Sci. USA 95: 12111–12116; Zhang, L., et al. (1998), Nucleic Acids Res. 26(16): 3687–3693; Zhang, J. K., et al (2000), Proc. Natl. Acad. Sci. USA 10.1073; Zhao, L., et al. (1998), J Am Chem Soc 120: 10256–10257; Ziermann, R., et al. (1999), Biotechniques 26: 106–110; Ziermann, R., et al. (2000), J Ind Microbial Biotech 24: 46–50; Gerth et al. 1996, J Antibiotics 49: 560–563; Bollag et al. 1995, Cancer Res. 55:2325–33; Hofle et al., 1996 "Epothilone A and B-novel 16-membered macrolides with cytotoxic activity: isolation, crystal structure, and conformation in solution, Angew. Chem. Int. Ed. Engl. 35:1567–1569; Su et al., 1997 "Structure-activity relationships of the epothilones and the first in vivo comparison with paclitaxel" Angew. Chem. Int. Ed. Engl. 36:2093–2096; Chou et al., 1998, "Desoxyepothilone B: an efficacious microtubule-targeted antitumor agent with a promising in vivo profile relative to epothilone B," Proc. Natl. Acad. Sci. USA 95: 9642–9647; PCT patent publication Nos. 00/00485, 99/67253, 99/67252, 99/65913, 99/54330, 99/54319, 99/54318, 99/43653, 99/43320, 99/42602, 99/40047, 99/27890, 99/07692, 99/02514, 99/01124, 98/25929, 98/22461, 98/08849, 97/19086; U.S. Pat. No. 5,969,145; and German patent publication No. DE 41 38 042.

SUMMARY OF THE INVENTION

In one aspect, the present invention provides recombinant methods and materials for genetically modifying a cell of the genus Sorangium (e.g., Sorangium cellulosum) using a transposon-based vector. Genetic modification in Sorangium using a transposon system has not previously been described. In an embodiment, the transposon-based vector contains a gene encoding a transposase, where transcription of the gene is under control of the E. coli bacteriophage T7A1 promoter.

In one aspect, the present invention provides recombinant methods and materials for genetically modifying a myxobacteria host cell, such as a Sorangium cell, using a transposase derived from the Chrysoperla carnea species of lacewing fly. In an embodiment, transcription of the Chrysoperla carnea transposase is under control of the T7A1 promoter In one embodiment, the invention is used for transforming and/or mutagenizing epothilone producing strains of Sorangium cellulosum. In one embodiment, the invention is directed to a method of mutagenizing Sorangium cellulosum to modify production of useful polyketides. In another embodiment, the invention is directed to a method of mutagenizing Sorangium cellulosum to produce epothilone compounds or analogs. In one embodiment, the invention is directed to a method of mutagenizing by transposon-mediated mutagenesis Sorangium cellulosum strain Soce90 or another epothilone A and/or B producing strain or species of Sorangium to inactivate the gene for the P450 cytochrome EpoK, encoded by the epoK gene, resulting in the accumulation of epothilones C and/or D instead of epothilones A and B. The invention also provides S. cellulosum host cells produced by the method, including S. cellulosum host cells that produce epothilones C and D but not epothilones B or A, and methods for fermenting such host cells to produce epothilones C and/or D.

In one embodiment, the invention provides novel transposase sequences, optionally under control of a T7A1 promoter, useful in mutagenizing organisms including Sorangium cellulosum and organisms other than Sorangium cellulosum (for instance, Stigmatella aurantiaca).

In one embodiment the invention is directed to a method of mutagenizing a Myxobacteria host cell to change the DNA in said cell. In one embodiment, the DNA changed encodes a polyketide synthase (PKS) or a non-ribosomal peptide synthase (NRPS) or a mixed PKS/NRPS gene cluster, and the mutagenized cell is fermented to produce useful compounds.

In one aspect, the invention provide a transposon-based vector useful for genetically modifying a host cell, e.g., a cell of the genus Sorangium (e.g., Sorangium cellulosum). In one embodiment, the vector comprises transposon inverted terminal repeat (ITR) nucleotide sequences flanking a marinar-type transposase gene sequence under the control of a T7A1 promoter. In another embodiment, the vector comprises transposon inverted terminal repeat (ITR) nucleotide sequences flanking a transposase gene sequence of SEQ ID NO:3, with the proviso that R1, R5 and R6 of said transposase gene sequence are not G nucleotides, and a selectable marker. In a related embodiment, R1 is A, and/or R5 is T, and/or R6 is C. In an embodiment, the transposase has a sequence of SEQ ID NO:2 or is an E137K variant thereof. In an embodiment, the transposase gene sequence is under the control of a T7A1 promoter. In an embodiment, the ITR sequences comprise

ACAGGTTGGCTGATAAGTCCCCGGTCTGGATCCA [SEQ ID NO:10]

GACCGGGGACTTATCAGCCAACCTGT.

In one embodiment, the invention provides materials and methods to insert a gene or genes into a host cell. In one embodiment, the inserted genes include an operon comprising a prpE gene, accA, and pccB genes to produce increased quantities of malonyl-CoA and/or methylmalonyl-CoA. The genes can be under the control of a suitable promoter, such as a PKS promoter, i.e. from epothilone (U.S. Pat. No. 6,303,342), soraphen (U.S. Pat. No. 5,716,849), or tombamycin (U.S. Pat. Nos. 6,280,999, and 6,090,601 and publication No. 20030054547A1), gene clusters. The gene or genes of interest are inserted between the inverted terminal repeats of transposon-based vector of the invention and transposed into the DNA of the host cell. In one embodiment of the invention, the genes are inserted into the S. cellulosum chromosome. In one embodiment the prpE gene is from Salmonella typhimurium. In one embodiment, the accA, and pccB genes are from Streptomyces coelicolor. In one embodiment the prpE gene, accA, and pccB genes are from Myxococcus xanthus. In another embodiment, the gene is a matB gene or is an operon comprising matB and matC genes, such as those from Rhizobium leguminosarum bv. trifolii, which respectively encode a ligase that can attach a CoA group to malonic or methylmalonic acid and a transporter molecule to transport malonic or methylmalonic acid into the host cell respectively, to produce increased quantities of malonyl-CoA and methylmalonyl-CoA. See U.S. patent application Ser. No. 09/687,855 (corresponding to WO 01/27306); Ser. No. 9/798,033 (corresponding to US20020045220A1); and Ser. No. 10/087,451.

In one aspect the invention provides a recombinant or isolated DNA comprising the sequence of SEQ ID NO:1. In one aspect the invention provides a recombinant or isolated DNA comprising the sequence of SEQ ID NO:3, optionally with the proviso that R1, R5 and R6 of said transposase gene sequence are not G nucleotides, optionally with the proviso that R1 is A, and/or R5 is T, and/or R6 is C. In one aspect the invention provides a recombinant or isolated polypeptide comprising the sequence of SEQ ID NO:2. In one aspect the invention provides a recombinant or isolated polypeptide comprising the sequence of SEQ ID NO:4. In one aspect, the invention provides a vector selected from the group consisting of pKOS183-3, pKOS183-132H, pKOS183-132B, and pKOS249-52B.

These and other embodiments of the invention are described in more detail in the following description, examples, and claims set forth below.

BRIEF DESCRIPTION OF THE DRAWINGS

FIG. 2 is the *C. carnea* transposase consensus double strand nucleotide sequence (SEQ ID NO:1) and translated amino acid sequence (SEQ ID NO:2).

FIG. 3 is the *C. carnea* transposase consensus double strand nucleotide sequence (SEQ ID NO. 3) and translated amino acid sequence (SEQ ID NO. 4) with ambiguity codes for mutations $R_1$ to $R_9$.

DETAILED DESCRIPTION OF THE INVENTION

Figure 1:
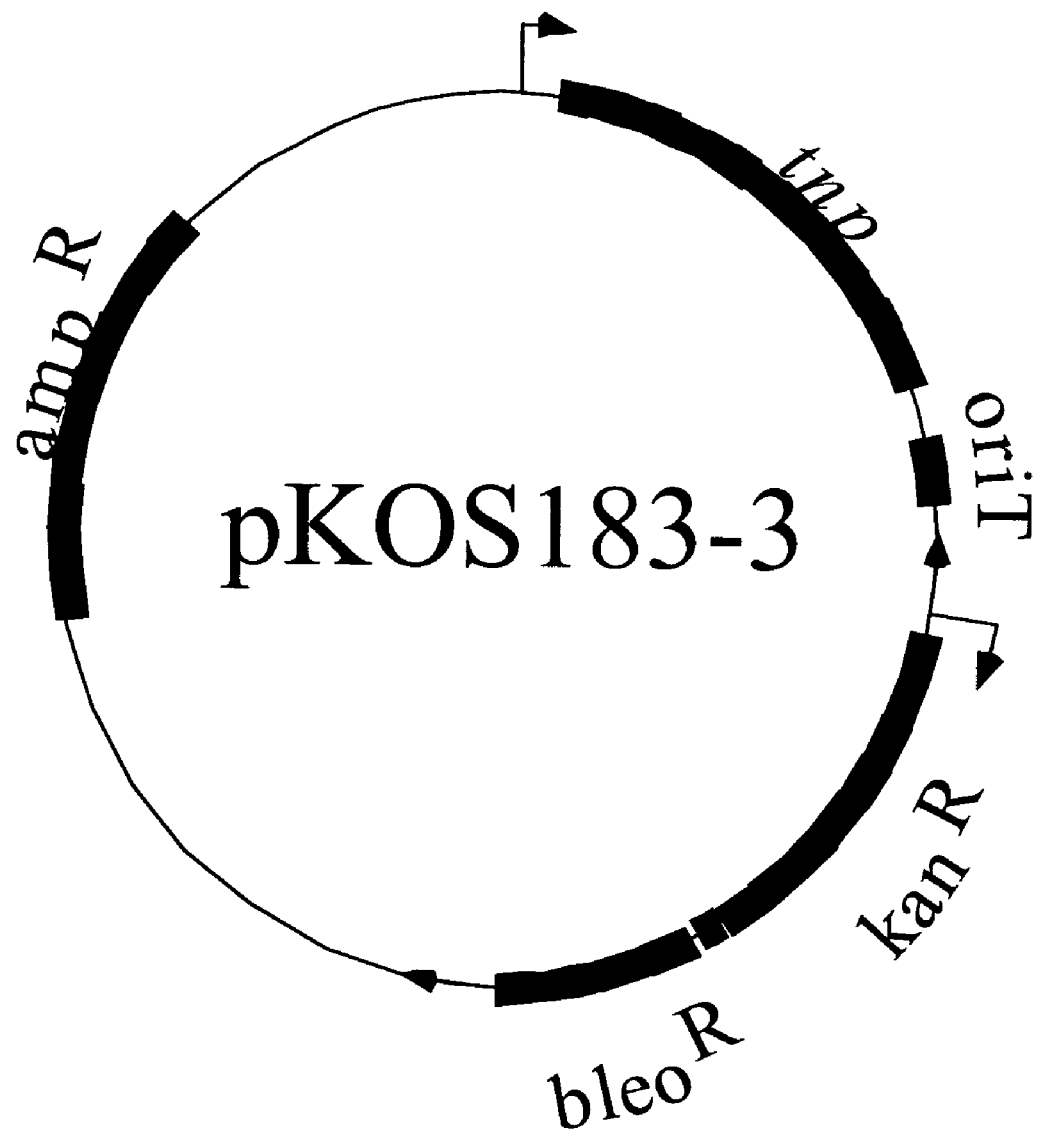
FIG. 1 is a schematic of plasmid pKOS183-3 with the *C. carnea* transposase tnp E137K, oriT, ampicillin, kanamycin and bleomycin resistance genes.

The present invention provides transposon-based genetic modification systems for *Sorangium* and other host cells of the order *Myxococcales*. Transposons, or transposable elements, are typically DNA sequences having a single open reading frame encoding a transposase protein flanked by two inverted terminal repeats (ITRs). As their name implies, they transpose themselves in the genome of the organism harboring them.

In one aspect the invention provides methods for altering deoxyribonucleic acid (DNA) in a *Sorangium* host cell includes transforming the cell with a transposon vector comprising inverted terminal repeat sequences (ITRs) and a gene encoding a transposase that recognizes the ITRs. The transposon vector transposes into said DNA, carrying with it any exogenous DNA that lies between the ITRs. As used herein, "transforming" refers to introducing an exogenous DNA into a cell, for example by conjugation from *E. coli* to *S. cellulosum* (or any host that is able to be conjugated with *E. coli*), electorporation, or other means.

In one aspect of the invention, the gene encoding the transposase is under control of the *E. coli* bacteriophage T7A1 promoter. This is a synthetic promoter that has two LacI binding sites that repress transcription. The T7A1 promoter is described in Lanzer et al., 1988, "Promoters largely determine the efficiency of repressor action" *Proc. Nat'l Acad Sci* 85:8973–77. Surprisingly, in *Sorangium* host cells, the activity of this heterologous promoter is sufficient to drive expression of transposase to achieve significant levels of transposition.

In one aspect of the invention, the methods of the invention utilize transposons of the mariner class (i.e., the vector encodes a mariner-type transposase). The mariner transposons are DNA-mediated transposons that encode transposases with a conserved motif in the catalytic domain of the protein (Doak et al., 1994, *Proc. Natl. Acad. Sci. USA* 91:942–46). Transposons of the mariner transposon class are widely distributed in animals (Zhang et al, 1998). Mariner transposons move through a DNA intermediate during transposition using a "cut-and-paste" mechanism, resulting in excision of the transposon from the original location and insertion at novel sites in the genome. Two essential components are necessary in this process, the active transposase and the ITRs that are recognized and mobilized by the transposase. Mariner transposons integrate into a thymidine-adenine (TA) target dinucleotide, which is duplicated upon insertion. With the mariner transposon, the transposase is sufficient to mediate transposition (Lampe et al., 1996). Mariner transposons do not rely on species-specific host factors, such as host rec proteins. Two transposons of the mariner class have been described as active in several hosts: the Mos1 mariner, isolated from *Drosophila mauritiana*, and Himar1 from the horn fly *Haematobia irritans*. Transposase mutants from the *Haematobia irritans* Himar1 element have been described in U.S. Pat. No. 6,368,830 B1.

In one aspect of the invention, the transposase is derived from a *Chrysoperla carnea* lacewing fly mariner transposon. Example 2 describes the cloning and characterization of this novel transposase (the "Carnea transposase"). In one embodiment, the transposase has an amino acid sequence of SEQ ID NO:2. In one embodiment, the transposase is encoded by a gene having (a) the nucleotide sequence of SEQ ID NO:1; (b) the nucleotide sequence of SEQ ID NO:3, with the proviso that R1, R5 and R6 are not G nucleotides; (c) the nucleotide sequence of SEQ ID NO:3, with the proviso that R1, R5 and R6 are not G nucleotides (d) the nucleotide sequence of SEQ ID NO:3 with the proviso that nucleotides at positions 409, 605 and 606 are adenine, thymidine, and cytosine respectively; or (e) an E137K variant of a, b, c, or d.

The vectors of the invention comprise (a) gene encoding a transposase (such as a mariner type transposase), driven by a promoter (such as the T7A1 promoter); (b) a nucleotide sequence of the inverted terminal repeats recognized by the transposase (such as the Himar 1 ITRs; see Robertson et al., 1995, "Recent horizontal transfer of a mariner transposable element among and between diptera and neuroptera" *Mol Biol. Evol.* 12:850–62) and optionally (c) selectable markers (such as markers that confer antibiotic resistance). The vector can also include the OriT sequence to enable conjugation from *E. coli* to the host.

The transposons of the present invention include transposons with enhanced transposition frequency. Transposition frequency is mediated by the activity of the transposase protein. Mutations in the transposase encoding region can lead to the mutants having increased transposition frequency. These mutations include those described in FIG. 3 and listed in SEQ ID NO:3. An illustrative double mutant, having a glutamic acid to lysine amino acid change at amino acid residue 137 and a phenylalanine to leucine change at amino acid residue 202, has increased transposition frequency compared to the SEQ ID NO:1 transposase.

In a different embodiment, the invention uses Tn5 transposon elements (Reznikoff et al. 1993, "The Tn5 transposon" *Annu Rev Microbiol.* 47:945–63). A minimal or basic transposon version of the Tn5 was also made, consisting of the Tn5 inverted terminal repeats nucleotide sequence and selectable markers (see Example 8). However, initial experiments with the Tn5 polymerase did not result in transposition. This may have been due to the absence of host factors.

In one aspect, the invention provides methods for introducing exogenous DNAs into host cells, e.g., *Myxoccocus*. In particular, methods and vectors disclosed herein have, surprisingly, been shown to result in genetic modifications in *Sorangium cellulosum* cells, and in one aspect, the invention provides methods for introducing exogenous DNAs into the chromosomes of cells of the suborder *Sorangineae*, especially *Sorangium*, and especially *Sorangium cellulosum* (e.g., So ce90 and SMP44 strains). *Myxococcales* comprises two suborders, the suborder Cystobacterineae, and the suborder Sorangineae. The suborder Sorangineae includes among other host cells of the present invention, the epothilone producer *Sorangium cellulosum*. The suborder Cystobacterineae includes the family Myxococcaceae and the family Cystobacteraceae. The family Myxococcacceae includes the genus *Angiococcus* (i.e., *A. disciforrmis*), the genus *Myxococcus*, and the genus *Corallococcus* (i.e., *C. macrosporus, C. corralloides*, and *C. exiguus*). The family Cystobacteraceae includes the genus *Cystobacter* (i.e., *C. fuscus, C. ferrugineus, C. minor, C. velatus*, and *C. violaceus*), the genus *Melittangium* (i.e., *M. boletus* and *M. lichenicola*), the genus *Stigmatella* (i.e., *S. erecta* and *S. aurantiaca*), and the genus *Archangium* (i.e., *A. gephyra*).

In one embodiment, the method of the present invention is applied to knock out genes in the epothilone producer *Sorangium cellulosum*. For illustration, in one embodiment, the methods are applied to knock out the epoK gene, or decrease activity of epoK, in an *S. cellulosum* host cell to create a host cell showing enhanced production of epothilone C and/or D. See U.S. Pat. No. 6,303,342. The invention also provides recombinant host cells produced by the method. This aspect of the invention is illustrated in (and without being limited by) Example 5, below.

The present invention can also be used to introduce genes to a host. For example, the transposons and methods of the present invention can be used to introduce new biosynthetic pathways into a host cell of the invention. This aspect of the invention is illustrated in Example 6 with respect to methods to increase epothilone production in certain host cells. Epothilone production requires the precursors malonyl-CoA (mCoA) and methylmalonyl-CoA (mmCoA). When methylmalonyl-CoA precursor pools are increased, this can result in increased production of epothilones in host cells in which these precursors are otherwise limiting production. Moreover, the ratio of mCoA and mmCoA in an epothilone producing host cell can influence the ratio of epothilone A and/or C production to epothilone B and/or D production due to the biochemical pathway by which these compounds are produced. By increasing the ratio of mmCo to mCoA, one can increase the ratio of epothilone B and D to epothilone A and C produced in host cells in which the amount of mmCoA is limiting the amount of epothilones B and D produced. Thus, if the epoK gene is also disrupted in such a host having excess methylmalonyl-CoA precursor, epothilone D will be the predominant product. The transposon of the present invention can be used to introduce genes, such as, for example, the matB and/or matC genes from *Rhizobium leguminosarum* bv *trifolrii*. MatB is a ligase that can attach a CoA group to malonic or methylmalonic acid. MatC is a transporter protein that can transport malonic or methylmalonic acid into the cell. Thus, by introducing these genes (matB alone may be sufficient) into a *Sorangium cellulosum* host cell having a disrupted epoK gene and in which precursor supply is limited, an increase in epothilone C and D can be observed. In one embodiment, the host cell into which exogenous DNAs is introduced according to the methods of the invention are cells that produce a polyketide at equal to or greater than 10 to 20 mg/L, more preferably at equal to or greater than 100 to 200 mg/L, and most preferably at equal to or greater than 1 to 2 g/L.

A detailed description of the invention having been provided, the following examples are given for the purpose of illustrating the invention and shall not be construed as being a limitation on the scope of the invention or claims.

EXAMPLE 1

Manipulation of DNA and Organisms (A) Strains. Routine DNA manipulations were performed in *Escherichia coli* XL1 Blue or *E. coli* XL1 Blue MR (Stratagene) & DH10B (BRL) using standard culture conditions (Sambrook et al., 1989). *Sorangium cellulosum* strain So ce90 was used for the transposon insertion.

(B) Manipulation of DNA and organisms. Manipulation and transformation of DNA in *E. coli* was performed according to standard procedures (Sambrook et al., 1989) or suppliers'protocols.

(C) DNA Sequencing and Analysis. PCR-based double-stranded DNA sequencing was performed on an Applied Biosystems (ABI) capillary sequencer using reagents and protocols provided by the manufacturer. Sequence was assembled using the SEQUENCHER (Gene Codes) software package and analyzed with MacVector (Oxford Molecular Group) and the NCBI BLAST.

(D) HPLC methods. Quantitation of polyketides was performed using a Hewlett-Packard 1090 HPLC equipped with a diode array detector and an Alltech 500 evaporative light scattering detector as described previously (Leaf et al., 2000, *Biotechnol. Prog.* 16: 553–556).

(E) Table 1 below shows illustrative plasmids, cosmids, and vectors of the present invention.

TABLE 1

| Plasmid name | Markers |
| --- | --- |
| pKOS183-3 | Tn Kan$^R$ Bleo$^R$ |
| pKOS183-132H | Tn Hyg$^R$ |
| pKOS183-132B | Tn Bleo$^R$ |
| pKOS249-52B | PT7AI E137K tnp + oriT + ITR +Bleo$^R$ |
| pKOS249-59.1 | tnp Bleo$^R$ (OE-IE Tn5) |
| pKOS249-59.2 | tnp Bleo$^R$ (OE-OE Tn5) |
| pKOS111-136.7 | PCR tnp (*C. carnea*) |
| pKOS111-137.9 | PCR tnp (*C. carnea*) |
| pKOS111-147 | Tnp 136.7 × 137.9 |
| pKOS111-158 | ITR |
| pKOS1II-160 | ITR |
| pKOS111-170 | ITR + Kan$^R$ Bleo$^R$ |
| pKOS111-179 | ITR + Kan$^R$ Bleo$^R$ + oriT |
| pKOS111-189.1 | "wt" tnp (*C. carnea*) |
| pKOS111-190 | PT7AI "wt" tnp (*C. carnea*) |
| pKOS183-70 | 20X up-mutant E137K tnp (*C. carnea*) |
| pKOS249-58.1 | Tn5 "wt" OE-IE (Tn5) |
| pKOS249-58.2 | Tn5 "wt" OE-OE Tn5) |
| PKOS249-57 | Tn5 OE-IE |

EXAMPLE 2

Cloning *Chrysoperla Carnea* Mariner Transposase Gene

The *Chrysoperla carnea* mariner transposase gene was isolated from the genome of the green lacewing fly *Chrysoperla carnea* by homology polymerase chain reaction amplification. Approximately 2000 *Chrysoperla carnea* lacewing fly eggs were obtained from Biocontrol Network (Brentwood, Tenn.), and the DNA isolated using the DNA isolation kit from Roche Molecular Biochemicals (Indianapolis, Ind.). After finishing the protocol as recommended, a phenol extraction followed by phenol/chloroform extraction of the DNA were carried out to further clean it up. Using the primers 111-132.5 (AACCATGGAAAAAAAG-GAATTTCGTGTTTT [SEQ ID NO:5]) and 111-132.6 (AAAAGCTTATTCAACATAGTTCCCTTCAAGAGC [SEQ ID NO:6]), the nucleotide sequence encoding the mariner transposase was amplified. The *Chrysoperla carnea* consensus sequence (see SEQ ID NO:1) encoding the transposase was derived from the PCR amplimers generated (which were designated 111-136.7 and 111-136.9). The resulting DNA fragment was cut with NcoI and HindIII, and ligated with pSL1190 (Pharmacia) cleaved with NcoI and HindIII.

Of 60 clones isolated, 15 were completely sequenced. Two clones, pKOS111-136.7 and pKOS111-136.9, contained several point mutations each and were further used to create a transposase gene with the consensus sequence. See FIG. 2 for the nucleotide and translated amino acid sequence of the *carnea* transposase (SEQ ID NOS: 1 and 2). A sequence listing standard ambiguity codes for various mutants of the present invention is described in FIG. 3 (SEQ ID NOS: 3 and 4).

The *C. carnea* consensus nucleotide sequence differs from the Himar1 sequence as described in Table 2 below (Row 1). Table 2 also shows the differences between the Himar1 sequence, sequences of clones 111-136.7 and 111-136.9, and the E137K mutant of *C. carnea* consensus sequences. The *C. carnea* consensus E137K mutant amino acid sequence differs from Himar1 sequence at amino acid residues 137 and 202, having a glutamic acid to lysine change at amino acid 137, and a tryptophan to phenylalanine change at amino acid 202. A modification of residue 137 of the Himar 1 sequence was reported to enhance transposition in *E. coli*.

TABLE 2

Comparison of *C. carnea* Transposase Sequences with Himar 1

| | | Nucleotide position | Amino Acid position | Amino Acid change |
|---|---|---|---|---|
| 1 | *C. carnea* consensus (SEQ ID NO:1) | 605,606 | 202 | W to F |
| 2 | E137K mutant (SEQ ID NO:3) | 409 | 137 | E to K |
| | | 605,606 | 202 | W to F |
| 3 | 111.136.7 | 453 | 151 | F to L |
| | | 485 | 162 | L to P |
| | | 917 | 306 | N to I |
| | | 932 | 311 | A to V |
| | | 966 | 322 | L to F |
| 4 | 111.136–9 | 449 | 150 | F to S |
| | | 453 | 151 | F to L |

EXAMPLE 3

Mariner-based Transposon Mutagenesis—Plasmid pKOS183-3

The basic transposon without the transposase gene was constructed by synthesizing an oligonucleotide containing the inverted repeats (111-158.1 CCGAATTCACAGGTTG-GCTGATAAGTCCCCGGTCTGGATCCA-GACCGGGGACTTATC AGCCAACCTGTGAATTCG [SEQ ID NO:11]. The oligonucleotide was denatured and annealed with itself, cleaved with EcoRI, and ligated into the EcoRI site of pBluescriptIISK+, to create plasmid pKOS111-158. Next, the inverted repeat was moved into pSL1190 by cleaving pKOS111-158 with EcoRI, isolating the 70 bp fragment and ligating with pSL1190 cleaved with EcoRI and MfeI to create pKOS111-160. The kanamycin and bleomycin resistance gene from Tn5 were inserted between the inverted repeats of the mariner ends by cleaving pBJ160 with BamHI, making the DNA ends blunt with the Klenow fragment of DNA polymerase I. This fragment was ligated with the kanamycin and bleomycin resistance marker that had been isolated on a~1.6 Kb EcoRI-BamHI fragment, the DNA ends made blunt, from pBJ180-1. The resulting plasmids, pKOS111-170.1.1 and pKOS111-170.1.2, are identical except they differ in the orientation of the resistance genes.

Next, the oriT region from RP4 was added to the two plasmids for the purpose of conjugating the final plasmids from *E. coli* to *S. cellulosum* or any host that is able to be conjugated with *E. coli*. First, the oriT region was isolated as a~400 BamHI-PstI fragment from pBJ183 and ligated with pSL1190 cleaved with BamHI and PstI to create pKOS111-163. Next, the mini mariner transposon with the kanamycin and bleomycin resistance genes was removed from either pKOS111-170.1.1 or pKOS111-170.1.2 as an EcoRI-EcoRV fragment and ligated with pKOS111-163 cleaved with EcoRI and SmaI. This results in plasmids pKOS111-179.1 and pKOS111-179.2.

Plasmid pKOS111-147 was constructed by isolating the small ClaI-HindIII fragment from pKOS111-136-9 and ligating it with the large ClaI-HindIII fragment of pKOS111-136-7. This removes non consensus nucleotides from the 3' end of the gene. The *C. carnea* consensus transposase was isolated by cleaving pKOS111-147 with NcoI and HpaI, isolating the ca. 400 bp fragment and ligating it into the NcoI and HpaI sites of pKOS111-161 resulting in plasmid pKOS111-189.1. To put the transposase gene downstream of the regulated T7A1 promoter, pKOS111-189.1 was cleaved with NcoI and HindIII and the 1.1 kb fragment was ligated with pUHE24-2B cleaved with NcoI and HindIII (plasmid pKOS111-190). Plasmid pUHE24-2B has the engineered T7A1 promoter (see Julien and Calender, 1995, "The purification and characterization of the bacteriophage P4Δ protein" *J. Bact.* 177:3743–51; Lanzer et al., 1988, "Promoters largely determine the efficiency of repressor action" *Proc. Nat'l Acad Sci* 85:8973–77).

The "mini mariner transposon" (comprising transposase, ITRs and antibiotic resistance) harboring the kanamycin and bleomycin resistance genes was cloned on the same plasmid as the transposase gene, pKOS111-179.1. Plasmid pKOS111-179.1 was cleaved with EcoRI, the DNA ends made blunt, and then cleaved with HindIII. The~2.1 Kb fragment was isolated and ligated with pKOS111-190, that had been cleaved with XbaI, the DNA ends made blunt, and cleaved with HindIII. The resulting plasmid, pKOS183.3, contains the *C. carnea* consensus mariner transposase sequence (see FIG. 2), the mini mariner transposon, and the oriT region. A second plasmid containing the lacI$^q$ gene is required in *E. coli* to repress the transcription of the transposase gene.

EXAMPLE 4

Transposon-Based Mutagenesis in *S. Cellulosum*

The plasmid pKOS183-3 vector described in Example 3, was used to mutagenize *S. cellulosum* strain So ce90, essentially according to the procedure described by Jaoua et al., 1992, *Plasmid* 28:157–65. The number of mutants generated ranged from 16,000 to 80,000 per conjugation. Since approximately $1 \times 10^9$ *S. cellulosum* cells were used for the conjugation, this translates into a transposition frequency of $1 \times 10^{-4}$ to $1 \times 10^{-5}$ per cell. The frequency of transposition did not change if the *S. cellulosum* cells were heat shocked at 50° C. for 10 minutes or if the *E. coli* strain harbored the dam and dcm mutations, genes required for methylating DNA. Either heat shock or the use of the methylation free *E.*

*coli* strain improves the efficiency of homologous recombination in *S. cellulosum*, but they appear not to be necessary for transposition (Jaoua et al., 1992; Pradella et al., 2002, "Characterisation, genome size and genetic manipulation of the myxobacterium *Sorangium cellulosum* So ce56" *Arch Microbiol* 178:484–92.

Figure 4:
FIG. 4 shows a Southern blot of transposon insertion strains. Lane 1. 1 kb ladder. Smallest band is 1.6 kb. Lanes 2–10. Nine independent transposon insertion strains.

To demonstrate that the phleomycin resistant colonies contained random insertions of transposon in the chromosome, DNA from nine isolates was analyzed by Southern blot. FIG. 4 shows the autoradiogram of chromosomal DNA cleaved with BamHI, a site not found within the transposon, and probed with the kanamycin and bleomycin resistance genes. The figure shows varying banding pattern for each isolate, indicating apparent random insertion into the chromosome. The parent strain does not contain a sequence that hybridizes to this probe and no antibiotic resistant colonies were obtained in the absence of the transposase gene.

EXAMPLE 5

Insertional Inactivation of EpoK Gene of *S. Cellulosum*

To demonstrate that the mariner transposon constructed had the potential to insert into a gene of interest, the 1260 bp epoK gene was chosen for targeting. This gene is a cytochrome P450 that adds an epoxide to epothilones C and D to make epothilones A and B, respectively (Julien et al., 2000, "Isolation and characterization of the epothilone biosynthetic gene cluster from *Sorangium cellulosum*" *Gene* 249:153–60). Insertions in epoK would provide an *S. cellulosum* strain that would produce epothilones C and D.

The *E. coli* strain DH10B harboring pKOS111-47, pGZ119EH, a lacI$^q$ plasmid, and pKOS183.3 was grown overnight without shaking at 37° C. to perform the conjugation with *S. cellulosum*. The strain Soce90 was grown in SYG to an OD$_{600}$ between 1 and 2, 5 ml of the culture was concentrated and the cells were mixed with the DH10B, pKOS111-47, pGZ119EH, that had been concentrated from 5 ml, in 200 µl of CYE or SYG medium. The *S. cellulosum* cells can also be heat shocked for 10 minutes at 50° C., as done for conjugations with *S. cellulosum*, before concentrating but this does not appear to increase transposition frequency. The mixture of cells were spotted onto an S42 plate and incubated at 30° C. for 24 hours. The cells were then scraped into 1 ml of SYG and 20–30 µl were plated onto S42 plates containing 50 µg/ml gentamycin and 30–60 µg/ml phleomycin. After approximately 7–10 days of incubation at 30–32° C., colonies were picked and restreaked onto S42 plates containing 30 µg/ml phleomycin.

Colonies that were phloemycin resistant and harboring epoK mutations were confirmed by PCR analysis or, alternatively, tested for the presence of epothilones by HPLC methods. PCR analysis was performed by using primers that flank the epoK gene, 178-164.1 (CCGCGTTCGAG-GCAAAATGATGGCAGCCTC [SEQ ID NO:7] and 178-164.2 (GGATTCGATCTTCGCGCGCTGACAATGGGC [SEQ ID NO:8]), and one for the transposon inverted repeat 183-47.15 (GGGGACTTATCAGCC-AACCTG [SEQ ID NO:9]).

Using the transposon, approximately 12,000 insertion mutant strains were generated in So ce90 and pools of 1000 mutants were grown in liquid medium. DNA was isolated from each of the pools and PCR reaction using primers annealing to the inverted repeat of the transposon and sequence upstream of epoK were performed. Five of the pools gave a PCR product. Sequencing of the PCR products showed that the transposon had inserted into 5 out of 21 TA sequences within the epoK gene, at nucleotides 277, 342, 377, 781, and 1016.

EXAMPLE 6

Increased Levels of Methylmalonyl-CoA

The pool of available methylmalonyl-CoA for the biosynthesis of epothilones is increased by inserting an additional source of cellular methylmalonyl CoA into a host cell. The host cell *S. cellulosum* produces both malonyl-CoA and methylmalonyl-CoA which are predicted to be synthesized using the accA and pccB genes, as has been reported for *M. xanthus*. The accA and pccB genes are PCR amplified and assembled into an operon along with a prpE gene, which encodes a propionyl CoA ligase, and a promoter from a PKS operon such as from the epothilone, soraphen, or tombamycin PKS gene clusters, located upstream of the genes. The synthetic operon is placed between the inverted repeats of the Tn5 or mariner transposon and transposed into the chromosomes of *S. cellulosum*. By increasing the input of starting materials into the epothilone biosynthesis pathway increased production of epothilones are obtained. Because epothilone D requires methylmalonyl-CoA for module 4 whereas epothilone C requires malonyl-CoA, the amount of epothilone D relative to epothilone C is thus increased. But because methylmalonyl-CoA is limiting, more epothilone C has been observed relative to epothilone D produced.

EXAMPLE 7

Introduction of Polyketide Precursor Biosynthesis Pathways in Host Cells

An alternative pathway for synthesis of malonyl-CoA and methylmalonyl-CoA is effectuated by the matB and matC gene products from *Rhizobium leguminosarum* bv, *trifolii*. MatB is a ligase that can attach a CoA group to malonic or methylmalonic acid. MatC is a transporter gene required to transport malonic or methyl malonic acid into the cell. The matB and matC genes are fused to an *S. cellulosum* promoter from the epothilone, soraphen, or tombamycin PKS gene clusters, and together placed between inverted repeats of the mariner transposon and transposed into the chromosome of *S. cellulosum*.

EXAMPLE 8

Minimal Tn5 Transposon for Use in *S. Cellulosum*

The wild type Tn5 transposon was transposed into the multicloning site of pBluescriptSKII+ to create plasmid vector pBJTn5. Plasmid vector pBJTn5 serves as a convenient vector for removing pieces of the transposon for construction of a minimal version. To isolate one of the inverted repeats, the inside end (IE), pBJTn5 is cleaved with PstI and PvuII and ligated into the PstI and StuI sites of pSL1190 (Amersham Pharmacia) to create pBJ101. To add the other inverted repeat and the tnp gene, pBJTn5 was cleaved with ApaI and BclI and the ca. 1500 bp fragment was ligated with pBJ100 cleaved with ApaI and BamHI to create pBJ101. A BamHI site was introduced by ligating a BamHI linker into the EcoRV site of pBJ101 to create pBJ102. This plasmid contains the basic requirements for transposition with the addition of an antibiotic resistance marker. This minimal transposon has been shown to work in *M. xanthus*.

In order to overexpress the tnp gene to get higher transposition frequency, the tnp gene is removed from pBJ102 by cleaving pBJ102 with EagI. The DNA ends are made blunt with the Klenow fragment of DNA polymerase I, and then cleaved with EcoRI. The~180 bp fragment, which contains the outside end (OE) is ligated into the BssHII site made blunt with the Klenow fragment of DNA polymerase I and EcoRI sites of pBJ1302. This results in a minimal miniTn5 transposon that contains one inside and one outside end of the inverted repeat.

The 1446 bp BspHI fragment from pBJ102 was ligated into the NcoI site of pUHE24-2Bf+ to create pBJ116, and so clone the tnp gene in a regulatable expression vector. In this plasmid, the Tn5 tnp gene is under the regulatable T7A1 promoter. There is a mutant form of the transposase protein that increases the transposition frequency. To construct this mutant, pRZ4857 was cleaved with HpaI and BglII and the 1330 bp fragment was ligated with pBJ116 cleaved with HpaI and BglII to create pBJ116*.

A mini transposon containing an OE and an IE for S. cellulosum was constructed by isolating the oriT fragment from pBJ183 as a BamHI PstI fragment, blunting the DNA ends made with the Klenow fragment of DNA polymerase I, and ligating into pBJ115 cleaved with ApaI site, which had the DNA ends made blunt with the Klenow fragment of DNA polymerase I, to make pKOS249-57. The hygromycin resistance marker was added to this plasmid by cleaving pKOS183-121 with BamHI and HindIII, the DNA ends were made blunt with the Klenow fragment of DNA polymerase I, and ligating the~1600 bp fragment into the SnaBI site I of pKOS249-57 to create pKOS249-58.

A minitransposon containing two OE ends, was made by cleaving pKOS249-58-1 with BstI Z17I. The resulting DNA ends are made blunt with the Klenow fragment of DNA polymerase I, and the oriT OE Hyg$^R$ fragment was ligated to pBJ115 cleaved with BstZ17I PstI and the DNA ends made blunt with the Klenow fragment of DNA polymerase I to create pKOS249-58-2. To add the tnp gene, pKOS249-58-2 was cleaved with BstBI and SpeI, the DNA ends made blunt with the Klenow fragment of DNA polymerase I and the oriT OE Hyg$^R$ OE fragment was ligated into either pBJ116* or pBJ116 cleaved with BamHI and XbaI, the DNA ends made blunt with the Klenow fragment of polymerase I to create pKOS249-59-2 & pKOS249-59-4, respectively.

To add either the wild type or mutated transposase genes to the mini Tn5 hygromycin construct, pKOS249-58 was cleaved with PstI and SmaI, the DNA ends were made blunt with the Klenow fragment of DNA polymerase I, and the miniTn5 hyg fragment was ligated into either pBJ116 or pBJ116* that had been cleaved with XbaI and BamHI and the DNA ends were made blunt with the Klenow fragment of DNA polymerase I to create pKOS249-59a and pKOS249-59b.

Both pKOS249-59a and pKOS249-59b are conjugated into S. cellulosum using established protocols and hygromycin resistant colonies are selected to test for transposition. In an initial experiment, no transposition was detected, perhaps due to the absence of host factors.

All publications and patent documents cited herein are incorporated herein by reference for all purposes, as if each such publication or document was specifically and individually indicated to be incorporated herein by reference. Although the present invention has been described in detail with reference to one or more specific embodiments, those of skill in the art will recognize that modifications and improvements are within the scope and spirit of the invention, as set forth in the claims which follow. Citation of publications and patent documents is not intended as an admission that any pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method of altering deoxyribonucleic acid (DNA) in a *Sorangium* host cell, said method comprising transforming said host cell with a mariner-type transposon vector comprising inverted terminal repeat sequences (ITRs) and a gene encoding a transposase that recognizes the ITRs, whereby the transposon vector transposes into said DNA.

2. The method of claim 1 wherein expression of the gene encoding the transposase is under control of a T7A1 promoter.

3. The method of claim 1 wherein the transposase is encoded by a gene isolated from a *Chrysoperla carnea* lacewing fly mariner transposon.

4. The method of claim 3 wherein the transposase has an amino acid sequence encoded by:
   (a) the nucleotide sequence of SEQ ID NO:1 except that the residue encoded at nucleotides 409–411 is lysine;
   (b) the nucleotide sequence of SEQ ID NO:3, with the proviso that R1, R5 and R6 are not G nucleotides;
   (c) the nucleotide sequence of SEQ ID NO:3, with the proviso that the residue encoded at nucleotides 409–411 is lysine;
   (d) the nucleotide sequence of SEQ ID NO:3 with the proviso that the nucleotide at position 509 is adenine, the nucleotide at position 605 is thymidine, and the nucleotide at position 606 is cytosine.

5. The method of claim 1 wherein the transposase has an amino acid sequence of SEQ ID NO:2.

6. The method of claim 5 wherein the gene encoding said transposase has the nucleotide sequence of SEQ ID NO:1.

7. The method of claim 3 wherein the gene encoding said transposase has the nucleotide sequence of SEQ ID NO:3 with the proviso that $R_1$, $R_5$ and $R_6$ are not G residues.

8. The method of claim 1, wherein said host cell is a *Sorangium cellulosum* host cell.

9. The method of claim 1 wherein said transposon vector transposes into said DNA and disrupts a gene contained in said DNA.

10. The method of claim 9, wherein said host cell is a *Sorangium cellulosum* host cell that produces epothilone A and B, and the gene that is disrupted is epoK, and the host cell no longer produces epothilone A or B after said transposition.

11. The method of claim 10, wherein said host cell produces epothilone C and D but not epothilone A and B after said transposition.

12. The method of claim 11, further comprising the step of culturing said host cell under conditions that lead to the production of epothilones C and D.

13. The method of claim 1 wherein said transposon vector transposes into said DNA at a location that does not disrupt a gene.

14. The method of claim 1 wherein said transposon vector comprises exogenous genes in addition to the transposase gene.

15. The method of claim 14 wherein the genes are selectable markers.

16. The method of claim 14, wherein said transforming results in introducing said exogenous genes into the genome of the host cell.

17. The method of claim 16, wherein said genes to be introduced into the host cell are selected from the group consisting of *Salmonella typhimurium* prpE, *Streptomyces coelicolor* accA, *Streytomyces coelicolor* pccB, *Rhizobium leguminosarum* bv. *trifolii* matB and *Rhizobium leguminosarum* bv. *trifolii* matC.

18. The method of claim 1, wherein said transposon terminal repeat sequences (ITRs) flank said gene encoding said transposase, wherein said transposase is a mariner-type transposase and said gene is under the control of a T7A1 promoter.

19. The method of claim 1, wherein said transposon terminal repeat sequences (ITRs) flank said gene encoding said transposase, wherein said gene comprises the nucleotide sequence of SEQ ID NO:3 with the proviso that $R_1$, $R_5$ and $R_6$ of said transposase gene sequence are not G residues, and said transposon vector further comprises a selectable marker.

20. The method of claim 19, wherein said transposase comprises the amino acid sequence of SEQ ID NO:2 or is an E137K variant thereof.

21. The method of claim 20, wherein said gene encoding said transposase is under the control of a T7A1 promoter.

22. The method of claim 19, wherein said transposon ITRs comprise the nucleotide sequence ACAGGTTGGCTGATAAGTCCCCGGTCTGGATCC AGACCGGGGACTTATCAGCCAACCTGT (SEQ ID NO:10).

* * * * *

SEQUENCE LISTING

<160> NUMBER OF SEQ ID NOS: 11

<210> SEQ ID NO 1
<211> LENGTH: 1047
<212> TYPE: DNA
<213> ORGANISM: Chrysoperla carnea
<220> FEATURE:
<221> NAME/KEY: CDS
<222> LOCATION: (1)...(1047)

<400> SEQUENCE: 1

```
atg gaa aaa aag gaa ttt cgt gtt ttg ata aaa tac tgt ttt ctg aag      48
Met Glu Lys Lys Glu Phe Arg Val Leu Ile Lys Tyr Cys Phe Leu Lys
 1               5                  10                  15 gga aaa aat aca gtg gaa gca aaa act tgg ctt gat aat gag ttt ccg      96
Gly Lys Asn Thr Val Glu Ala Lys Thr Trp Leu Asp Asn Glu Phe Pro
             20                  25                  30 gac tct gcc cca ggg aaa tca aca ata att gat tgg tat gca aaa ttc     144
Asp Ser Ala Pro Gly Lys Ser Thr Ile Ile Asp Trp Tyr Ala Lys Phe
         35                  40                  45 aag cgt ggt gaa atg agc acg gag gac ggt gaa cgc agt gga cgc ccg     192
Lys Arg Gly Glu Met Ser Thr Glu Asp Gly Glu Arg Ser Gly Arg Pro
     50                  55                  60
```

-continued

| | | |
|---|---|---|
| aaa gag gtg gtt acc gac gaa aac atc aaa aaa atc cac aaa atg att<br>Lys Glu Val Val Thr Asp Glu Asn Ile Lys Lys Ile His Lys Met Ile<br>65                         70                          75                         80 | 240 |
| ttg aat gac cgt aaa atg aag ttg atc gag ata gca gag gcc tta aag<br>Leu Asn Asp Arg Lys Met Lys Leu Ile Glu Ile Ala Glu Ala Leu Lys<br>                    85                          90                         95 | 288 |
| ata tca aag gaa cgt gtt ggt cat atc att cat caa tat ttg gat atg<br>Ile Ser Lys Glu Arg Val Gly His Ile Ile His Gln Tyr Leu Asp Met<br>                100                       105                      110 | 336 |
| cgg aag ctc tgt gca aaa tgg gtg ccg cgc gag ctc aca ttt gac caa<br>Arg Lys Leu Cys Ala Lys Trp Val Pro Arg Glu Leu Thr Phe Asp Gln<br>             115                    120                       125 | 384 |
| aaa caa caa cgt gtt gat gat tct gag cgg tgt ttg cag ctg tta act<br>Lys Gln Gln Arg Val Asp Asp Ser Glu Arg Cys Leu Gln Leu Leu Thr<br>130                        135                         140 | 432 |
| cgt aat aca ccc gag ttt ttc cgt cga tat gtg aca atg gat gaa aca<br>Arg Asn Thr Pro Glu Phe Phe Arg Arg Tyr Val Thr Met Asp Glu Thr<br>145                         150                       155                   160 | 480 |
| tgg ctc cat cac tac act cct gag tcc aat cga cag tcg gct gag tgg<br>Trp Leu His His Tyr Thr Pro Glu Ser Asn Arg Gln Ser Ala Glu Trp<br>                         165                       170                  175 | 528 |
| aca gcg acc ggt gaa ccg tct ccg aag cgt gga aag act caa aag tcc<br>Thr Ala Thr Gly Glu Pro Ser Pro Lys Arg Gly Lys Thr Gln Lys Ser<br>             180                    185                       190 | 576 |
| gct ggc aaa gta atg gcc tct gtt ttt ttc gat gcg cat gga ata att<br>Ala Gly Lys Val Met Ala Ser Val Phe Phe Asp Ala His Gly Ile Ile<br>             195                    200                     205 | 624 |
| ttt atc gat tat ctt gag aag gga aaa acc atc aac agt gac tat tat<br>Phe Ile Asp Tyr Leu Glu Lys Gly Lys Thr Ile Asn Ser Asp Tyr Tyr<br>210                        215                        220 | 672 |
| atg gcg tta ttg gag cgt ttg aag gtc gaa atc gcg gca aaa cgg ccc<br>Met Ala Leu Leu Glu Arg Leu Lys Val Glu Ile Ala Ala Lys Arg Pro<br>225                        230                       235                   240 | 720 |
| cat atg aag aag aaa aaa gtg ttg ttc cac caa gac aac gca ccg tgc<br>His Met Lys Lys Lys Lys Val Leu Phe His Gln Asp Asn Ala Pro Cys<br>                        245                       250                   255 | 768 |
| cac aag tca ttg aga acg atg gca aaa att cat gaa ttg ggc ttc gaa<br>His Lys Ser Leu Arg Thr Met Ala Lys Ile His Glu Leu Gly Phe Glu<br>             260                    265                       270 | 816 |
| ttg ctt ccc cac cca ccg tat tct cca gat ctg gcc ccc agc gac ttt<br>Leu Leu Pro His Pro Pro Tyr Ser Pro Asp Leu Ala Pro Ser Asp Phe<br>             275                    280                       285 | 864 |
| ttc ttg ttc tca gac ctc aaa agg atg ctc gca ggg aaa aaa ttt ggc<br>Phe Leu Phe Ser Asp Leu Lys Arg Met Leu Ala Gly Lys Lys Phe Gly<br>290                        295                        300 | 912 |
| tgc aat gaa gag gtg atc gcc gaa act gag gcc tat ttt gag gca aaa<br>Cys Asn Glu Glu Val Ile Ala Glu Thr Glu Ala Tyr Phe Glu Ala Lys<br>305                        310                       315                   320 | 960 |
| ccg aag gag tac tac caa aat ggt atc aaa aaa ttg gaa ggt cgt tat<br>Pro Lys Glu Tyr Tyr Gln Asn Gly Ile Lys Lys Leu Glu Gly Arg Tyr<br>                         325                       330                  335 | 1008 |
| aat cgt tgt atc gct ctt gaa ggg aac tat gtt gaa taa<br>Asn Arg Cys Ile Ala Leu Glu Gly Asn Tyr Val Glu *<br>             340                    345 | 1047 |

<210> SEQ ID NO 2
<211> LENGTH: 348
<212> TYPE: PRT
<213> ORGANISM: Chrysoperla carnea

<400> SEQUENCE: 2

```
Met Glu Lys Lys Glu Phe Arg Val Leu Ile Lys Tyr Cys Phe Leu Lys
 1               5                  10                  15

Gly Lys Asn Thr Val Glu Ala Lys Thr Trp Leu Asp Asn Glu Phe Pro
             20                  25                  30

Asp Ser Ala Pro Gly Lys Ser Thr Ile Ile Asp Trp Tyr Ala Lys Phe
         35                  40                  45

Lys Arg Gly Glu Met Ser Thr Glu Asp Gly Glu Arg Ser Gly Arg Pro
     50                  55                  60

Lys Glu Val Val Thr Asp Glu Asn Ile Lys Ile His Lys Met Ile
 65                  70                  75                  80

Leu Asn Asp Arg Lys Met Lys Leu Ile Glu Ile Ala Glu Ala Leu Lys
                 85                  90                  95

Ile Ser Lys Glu Arg Val Gly His Ile Ile His Gln Tyr Leu Asp Met
            100                 105                 110

Arg Lys Leu Cys Ala Lys Trp Val Pro Arg Glu Leu Thr Phe Asp Gln
        115                 120                 125

Lys Gln Gln Arg Val Asp Asp Ser Glu Arg Cys Leu Gln Leu Leu Thr
    130                 135                 140

Arg Asn Thr Pro Glu Phe Phe Arg Arg Tyr Val Thr Met Asp Glu Thr
145                 150                 155                 160

Trp Leu His His Tyr Thr Pro Glu Ser Asn Arg Gln Ser Ala Glu Trp
                165                 170                 175

Thr Ala Thr Gly Glu Pro Ser Pro Lys Arg Gly Lys Thr Gln Lys Ser
            180                 185                 190

Ala Gly Lys Val Met Ala Ser Val Phe Phe Asp Ala His Gly Ile Ile
        195                 200                 205

Phe Ile Asp Tyr Leu Glu Lys Gly Lys Thr Ile Asn Ser Asp Tyr Tyr
    210                 215                 220

Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
                245                 250                 255

His Lys Ser Leu Arg Thr Met Ala Lys Ile His Glu Leu Gly Phe Glu
            260                 265                 270

Leu Leu Pro His Pro Pro Tyr Ser Pro Asp Leu Ala Pro Ser Asp Phe
        275                 280                 285

Phe Leu Phe Ser Asp Leu Lys Arg Met Leu Ala Gly Lys Lys Phe Gly
    290                 295                 300

Cys Asn Glu Glu Val Ile Ala Glu Thr Glu Ala Tyr Phe Glu Ala Lys
305                 310                 315                 320

Pro Lys Glu Tyr Tyr Gln Asn Gly Ile Lys Lys Leu Glu Gly Arg Tyr
                325                 330                 335

Asn Arg Cys Ile Ala Leu Glu Gly Asn Tyr Val Glu
            340                 345
```

<210> SEQ ID NO 3
<211> LENGTH: 1047
<212> TYPE: DNA
<213> ORGANISM: Chrysoperla carnea
<220> FEATURE:
<221> NAME/KEY: CDS
<222> LOCATION: (1)...(1047)
<220> FEATURE:
<221> NAME/KEY: misc_feature
<222> LOCATION: 137

```
<223> OTHER INFORMATION: Xaa = Glu or Lys
<220> FEATURE:
<221> NAME/KEY: misc_feature
<222> LOCATION: 150
<223> OTHER INFORMATION: Xaa = Phe or Ser
<220> FEATURE:
<221> NAME/KEY: misc_feature
<222> LOCATION: 151
<223> OTHER INFORMATION: Xaa = Phe or Leu
<220> FEATURE:
<221> NAME/KEY: misc_feature
<222> LOCATION: 162
<223> OTHER INFORMATION: Xaa = Leu or Pro
<220> FEATURE:
<221> NAME/KEY: misc_feature
<222> LOCATION: 202
<223> OTHER INFORMATION: Xaa = Trp or Phe
<220> FEATURE:
<221> NAME/KEY: misc_feature
<222> LOCATION: 306
<223> OTHER INFORMATION: Xaa = Asn or Ile
<220> FEATURE:
<221> NAME/KEY: misc_feature
<222> LOCATION: 311
<223> OTHER INFORMATION: Xaa = Ala or Val

<400> SEQUENCE: 3 atg gaa aaa aag gaa ttt cgt gtt ttg ata aaa tac tgt ttt ctg aag     48
Met Glu Lys Lys Glu Phe Arg Val Leu Ile Lys Tyr Cys Phe Leu Lys
1               5                   10                  15 gga aaa aat aca gtg gaa gca aaa act tgg ctt gat aat gag ttt ccg     96
Gly Lys Asn Thr Val Glu Ala Lys Thr Trp Leu Asp Asn Glu Phe Pro
            20                  25                  30 gac tct gcc cca ggg aaa tca aca ata att gat tgg tat gca aaa ttc    144
Asp Ser Ala Pro Gly Lys Ser Thr Ile Ile Asp Trp Tyr Ala Lys Phe
        35                  40                  45 aag cgt ggt gaa atg agc acg gag gac ggt gaa cgc agt gga cgc ccg    192
Lys Arg Gly Glu Met Ser Thr Glu Asp Gly Glu Arg Ser Gly Arg Pro
    50                  55                  60 aaa gag gtg gtt acc gac gaa aac atc aaa aaa atc cac aaa atg att    240
Lys Glu Val Val Thr Asp Glu Asn Ile Lys Lys Ile His Lys Met Ile
65                  70                  75                  80 ttg aat gac cgt aaa atg aag ttg atc gag ata gca gag gcc tta aag    288
Leu Asn Asp Arg Lys Met Lys Leu Ile Glu Ile Ala Glu Ala Leu Lys
                85                  90                  95 ata tca aag gaa cgt gtt ggt cat atc att cat caa tat ttg gat atg    336
Ile Ser Lys Glu Arg Val Gly His Ile Ile His Gln Tyr Leu Asp Met
            100                 105                 110 cgg aag ctc tgt gca aaa tgg gtg ccg cgc gag ctc aca ttt gac caa    384
Arg Lys Leu Cys Ala Lys Trp Val Pro Arg Glu Leu Thr Phe Asp Gln
        115                 120                 125 aaa caa caa cgt gtt gat gat tct rag cgg tgt ttg cag ctg tta act    432
Lys Gln Gln Arg Val Asp Asp Ser Xaa Arg Cys Leu Gln Leu Leu Thr
    130                 135                 140 cgt aat aca ccc gag tyt tts cgt cga tat gtg aca atg gat gaa aca    480
Arg Asn Thr Pro Glu Xaa Xaa Arg Arg Tyr Val Thr Met Asp Glu Thr
145                 150                 155                 160 tgg cyc cat cac tac act cct gag tcc aat cga cag tcg gct gag tgg    528
Trp Xaa His His Tyr Thr Pro Glu Ser Asn Arg Gln Ser Ala Glu Trp
                165                 170                 175 aca gcg acc ggt gaa ccg tct ccg aag cgt gga aag act caa aag tcc    576
Thr Ala Thr Gly Glu Pro Ser Pro Lys Arg Gly Lys Thr Gln Lys Ser
            180                 185                 190 gct ggc aaa gta atg gcc tct gtt ttt tks gat gcg cat gga ata att    624
Ala Gly Lys Val Met Ala Ser Val Phe Xaa Asp Ala His Gly Ile Ile
        195                 200                 205
```

```
ttt atc gat tat ctt gag aag gga aaa acc atc aac agt gac tat tat      672
Phe Ile Asp Tyr Leu Glu Lys Gly Lys Thr Ile Asn Ser Asp Tyr Tyr
    210                 215                 220 atg gcg tta ttg gag cgt ttg aag gtc gaa atc gcg gca aaa cgg ccc      720
Met Ala Leu Leu Glu Arg Leu Lys Val Glu Ile Ala Ala Lys Arg Pro
225                 230                 235                 240 cat atg aag aag aaa aaa gtg ttg ttc cac caa gac aac gca ccg tgc      768
His Met Lys Lys Lys Lys Val Leu Phe His Gln Asp Asn Ala Pro Cys
                245                 250                 255 cac aag tca ttg aga acg atg gca aaa att cat gaa ttg ggc ttc gaa      816
His Lys Ser Leu Arg Thr Met Ala Lys Ile His Glu Leu Gly Phe Glu
            260                 265                 270 ttg ctt ccc cac cca ccg tat tct cca gat ctg gcc ccc agc gac ttt      864
Leu Leu Pro His Pro Pro Tyr Ser Pro Asp Leu Ala Pro Ser Asp Phe
        275                 280                 285 ttc ttg ttc tca gac ctc aaa agg atg ctc gca ggg aaa aaa ttt ggc      912
Phe Leu Phe Ser Asp Leu Lys Arg Met Leu Ala Gly Lys Lys Phe Gly
    290                 295                 300 tgc awt gaa gag gtg atc gyc gaa act gag gcc tat ttt gag gca aaa      960
Cys Xaa Glu Glu Val Ile Xaa Glu Thr Glu Ala Tyr Phe Glu Ala Lys
305                 310                 315                 320 ccg aar gag tac tac caa aat ggt atc aaa aaa ttg gaa ggt cgt tat     1008
Pro Lys Glu Tyr Tyr Gln Asn Gly Ile Lys Lys Leu Glu Gly Arg Tyr
                325                 330                 335 aat cgt tgt atc gct ctt gaa ggg aac tat gtt gaa taa                 1047
Asn Arg Cys Ile Ala Leu Glu Gly Asn Tyr Val Glu *
            340                 345

<210> SEQ ID NO 4
<211> LENGTH: 348
<212> TYPE: PRT
<213> ORGANISM: Chrysoperla carnea
<220> FEATURE:
<221> NAME/KEY: VARIANT
<222> LOCATION: 137
<223> OTHER INFORMATION: Xaa = Glu or Lys
<220> FEATURE:
<221> NAME/KEY: VARIANT
<222> LOCATION: 150
<223> OTHER INFORMATION: Xaa = Phe or Ser
<220> FEATURE:
<221> NAME/KEY: VARIANT
<222> LOCATION: 151
<223> OTHER INFORMATION: Xaa = Phe or Leu
<220> FEATURE:
<221> NAME/KEY: VARIANT
<222> LOCATION: 162
<223> OTHER INFORMATION: Xaa = Leu or Pro
<220> FEATURE:
<221> NAME/KEY: VARIANT
<222> LOCATION: 202
<223> OTHER INFORMATION: Xaa = Trp or Phe
<220> FEATURE:
<221> NAME/KEY: VARIANT
<222> LOCATION: 306
<223> OTHER INFORMATION: Xaa = Asn or Ile
<220> FEATURE:
<221> NAME/KEY: VARIANT
<222> LOCATION: 311
<223> OTHER INFORMATION: Xaa = Ala or Val

<400> SEQUENCE: 4

Met Glu Lys Lys Glu Phe Arg Val Leu Ile Lys Tyr Cys Phe Leu Lys
  1               5                  10                  15

Gly Lys Asn Thr Val Glu Ala Lys Thr Trp Leu Asp Asn Glu Phe Pro
            20                  25                  30
```

```
Asp Ser Ala Pro Gly Lys Ser Thr Ile Ile Asp Trp Tyr Ala Lys Phe
        35                  40                  45
Lys Arg Gly Glu Met Ser Thr Glu Asp Gly Glu Arg Ser Gly Arg Pro
    50                  55                  60
Lys Glu Val Val Thr Asp Glu Asn Ile Lys Lys Ile His Lys Met Ile
65                  70                  75                  80
Leu Asn Asp Arg Lys Met Lys Leu Ile Glu Ile Ala Glu Ala Leu Lys
                85                  90                  95
Ile Ser Lys Glu Arg Val Gly His Ile Ile His Gln Tyr Leu Asp Met
            100                 105                 110
Arg Lys Leu Cys Ala Lys Trp Val Pro Arg Glu Leu Thr Phe Asp Gln
        115                 120                 125
Lys Gln Gln Arg Val Asp Asp Ser Xaa Arg Cys Leu Gln Leu Leu Thr
    130                 135                 140
Arg Asn Thr Pro Glu Xaa Xaa Arg Arg Tyr Val Thr Met Asp Glu Thr
145                 150                 155                 160
Trp Xaa His His Tyr Thr Pro Glu Ser Asn Arg Gln Ser Ala Glu Trp
                165                 170                 175
Thr Ala Thr Gly Glu Pro Ser Pro Lys Arg Gly Lys Thr Gln Lys Ser
            180                 185                 190
Ala Gly Lys Val Met Ala Ser Val Phe Xaa Asp Ala His Gly Ile Ile
        195                 200                 205
Phe Ile Asp Tyr Leu Glu Lys Gly Lys Thr Ile Asn Ser Asp Tyr Tyr
    210                 215                 220
Met Ala Leu Leu Glu Arg Leu Lys Val Glu Ile Ala Ala Lys Arg Pro
225                 230                 235                 240
His Met Lys Lys Lys Val Leu Phe His Gln Asp Asn Ala Pro Cys
                245                 250                 255
His Lys Ser Leu Arg Thr Met Ala Lys Ile His Glu Leu Gly Phe Glu
            260                 265                 270
Leu Leu Pro His Pro Pro Tyr Ser Pro Asp Leu Ala Pro Ser Asp Phe
        275                 280                 285
Phe Leu Phe Ser Asp Leu Lys Arg Met Leu Ala Gly Lys Lys Phe Gly
    290                 295                 300
Cys Xaa Glu Glu Val Ile Xaa Glu Thr Glu Ala Tyr Phe Glu Ala Lys
305                 310                 315                 320
Pro Lys Glu Tyr Tyr Gln Asn Gly Ile Lys Lys Leu Glu Gly Arg Tyr
                325                 330                 335
Asn Arg Cys Ile Ala Leu Glu Gly Asn Tyr Val Glu
            340                 345

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
aaccatggaa aaaaggaat ttcgtgtttt                                    30

<210> SEQ ID NO 6
<211> LENGTH: 33
<212> TYPE: DNA
<213> ORGANISM: Artificial Sequence
<220> FEATURE:
<223> OTHER INFORMATION: Synthetic Construct
```

```
<400> SEQUENCE: 6
aaaagcttat tcaacatagt tcccttcaag agc                                    33

<210> SEQ ID NO 7
<211> LENGTH: 30
<212> TYPE: DNA
<213> ORGANISM: Artificial Sequence
<220> FEATURE:
<223> OTHER INFORMATION: Synthetic Construct

<400> SEQUENCE: 7
ccgcgttcga ggcaaaatga tggcagcctc                                        30

<210> SEQ ID NO 8
<211> LENGTH: 30
<212> TYPE: DNA
<213> ORGANISM: Artificial Sequence
<220> FEATURE:
<223> OTHER INFORMATION: Synthetic Construct

<400> SEQUENCE: 8
ggattcgatc ttcgcgcgct gacaatgggc                                        30

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
ggggacttat cagccaacct g                                                 21

<210> SEQ ID NO 10
<211> LENGTH: 60
<212> TYPE: DNA
<213> ORGANISM: Artificial Sequence
<220> FEATURE:
<223> OTHER INFORMATION: Synthetic Construct

<400> SEQUENCE: 10
acaggttggc tgataagtcc ccggtctgga tccagaccgg ggacttatca gccaacctgt        60

<210> SEQ ID NO 11
<211> LENGTH: 75
<212> TYPE: DNA
<213> ORGANISM: Artificial Sequence
<220> FEATURE:
<223> OTHER INFORMATION: Synthetic Construct

<400> SEQUENCE: 11
ccgaattcac aggttggctg ataagtcccc ggtctggatc cagaccgggg acttatcagc        60
caacctgtga attcg                                                        75
```